United States Patent
Bolla

(10) Patent No.: US 10,201,448 B2
(45) Date of Patent: Feb. 12, 2019

(54) PALMAR THUMB AND THUMB SADDLE JOINT SPLINT

(75) Inventor: Kalman Bolla, Neuhausen am Rheinfall (CH)

(73) Assignee: Chrisofix AG, Neuhausen am Rheinfall (CH)

( * ) Notice: Subject to any disclaimer, the term of this patent is extended or adjusted under 35 U.S.C. 154(b) by 1470 days.

(21) Appl. No.: 13/583,867

(22) PCT Filed: Feb. 22, 2011

(86) PCT No.: PCT/EP2011/052603
§ 371 (c)(1),
(2), (4) Date: Oct. 12, 2012

(87) PCT Pub. No.: WO2011/110420
PCT Pub. Date: Sep. 15, 2011

(65) Prior Publication Data
US 2013/0197411 A1    Aug. 1, 2013

(30) Foreign Application Priority Data
Mar. 8, 2010   (CH) .......................... 302/10

(51) Int. Cl.
*A61F 5/058* (2006.01)
*A61F 5/01* (2006.01)

(52) U.S. Cl.
CPC ........ *A61F 5/05866* (2013.01); *A61F 5/0118* (2013.01)

(58) Field of Classification Search
CPC .......... A61F 5/10; A61F 5/37; A61F 5/05866; A61F 5/05875; A61F 5/0118
USPC .............. 128/869, 878–880, 881; 602/21–22
See application file for complete search history.

(56) References Cited

U.S. PATENT DOCUMENTS

| | | | | |
|---|---|---|---|---|
| 3,124,127 | A | * | 3/1964 | Ruuska ............... A61F 5/05866 602/21 |
| 3,618,557 | A | * | 11/1971 | Merriman ....................... 116/86 |
| 4,124,185 | A | * | 11/1978 | Preisinger ....................... 248/98 |
| 4,438,532 | A | * | 3/1984 | Campanella et al. ............. 2/16 |

(Continued)

FOREIGN PATENT DOCUMENTS

| | | | | |
|---|---|---|---|---|
| CH | 690 954 A5 | | 3/2001 | |
| CH | 702 784 A1 | * | 9/2011 | ............. A61F 13/10 |

(Continued)

*Primary Examiner* — Kari Rodriquez
*Assistant Examiner* — Camtu Nguyen
(74) *Attorney, Agent, or Firm* — Pauley Erickson & Kottis

(57) ABSTRACT

A palmar thumb and thumb saddle joint splint comprises a first splint part for receiving the thumb and means for fastening the first splint part to the hand. The first splint part formed as a shell part that is open at the top and is intrinsically stiff but deformable, in which shell part the thumb is laid; the first splint plant being connected firmly to a side-of-the-hand part that is intrinsically stiff but deformable and, when the splint is put in place, embraces the side of the splinted hand; and the fastening means comprising first and second fixing strips which are intrinsically stiff but deformable, wherein the first fixing strip runs from the side-of-the-hand part over the back of the hand to the first splint part, and the second fixing strip, starting from the side of the hand part, is led through between thumb and index finger to the first splint part.

9 Claims, 3 Drawing Sheets

(56) References Cited

U.S. PATENT DOCUMENTS

| | | | | |
|---|---|---|---|---|
| 4,506,663 | A | * | 3/1985 | Baron ................... A61F 13/02 128/880 |
| 4,524,464 | A | * | 6/1985 | Primiano ......... A41D 19/015 88 128/879 |
| 4,549,537 | A | * | 10/1985 | Ender ................ A61F 5/05866 602/21 |
| 4,658,441 | A | * | 4/1987 | Smith .................. A41D 13/087 2/16 |
| 4,953,568 | A | * | 9/1990 | Theisler ............... A61F 13/105 128/878 |
| 5,188,356 | A | * | 2/1993 | Furr .................. A63B 69/0071 128/880 |
| 5,409,451 | A | * | 4/1995 | Daneman ........... A61F 5/05866 602/20 |
| 5,515,870 | A | * | 5/1996 | Zilber ..................... A61F 5/50 128/878 |
| 5,637,078 | A | * | 6/1997 | Varn .............................. 602/21 |
| 5,713,836 | A | * | 2/1998 | O'keefe ............ A61F 5/05858 602/20 |
| 5,746,707 | A | * | 5/1998 | Eck ................................ 602/21 |
| 5,787,896 | A | * | 8/1998 | Sackett ................ A61F 5/0118 128/880 |
| 5,890,228 | A | * | 4/1999 | Wagner ............................ 2/160 |
| 5,899,870 | A | * | 5/1999 | Deirmendjian ....... A61F 13/104 128/880 |
| 6,146,347 | A | | 11/2000 | Porrata |
| 6,261,252 | B1 | * | 7/2001 | Darcey ............... A61F 5/05866 602/5 |
| 6,520,925 | B1 | | 2/2003 | Thibodo, Jr. |
| 6,702,772 | B1 | | 3/2004 | Colditz |
| 6,783,507 | B1 | * | 8/2004 | Fisher .................. A61F 5/0118 602/21 |
| 7,537,577 | B2 | * | 5/2009 | Phelan .................. A61F 5/0118 128/878 |
| 2006/0149180 | A1 | * | 7/2006 | Phelen .................. A61F 5/0118 602/20 |
| 2012/0179081 | A1 | * | 7/2012 | Anglada ............... A61F 5/0118 602/21 |
| 2015/0157483 | A1 | * | 6/2015 | Grunden ................ A61F 5/013 602/22 |

FOREIGN PATENT DOCUMENTS

| | | | | |
|---|---|---|---|---|
| DE | | 35 19 493 A1 | 12/1896 | |
| DE | | 30 06 362 A1 | 8/1981 | |
| DE | | 35 19 493 A1 | 12/1986 | |
| EP | | 0 143 348 A1 | 6/1985 | |
| WO | WO 96/27349 A1 | | 9/1996 | |
| WO | WO 97/22312 | * | 6/1997 | |
| WO | WO 03/017887 A1 | | 3/2003 | |
| WO | WO 2007/066367 A2 | | 6/2007 | |
| WO | WO 2010/137193 A1 | * | 12/2009 | |
| WO | WO2010/137193 A1 | * | 12/2010 | ............ A44B 19/10 |

* cited by examiner

PALMAR THUMB AND THUMB SADDLE JOINT SPLINT

BACKGROUND OF THE INVENTION

Field of the Invention

The present invention relates to the field of medical splints. It concerns a palmar thumb and thumb saddle joint splint as recited in the preamble to claim 1.

Discussion of Related Art

The thumb of the human hand has a high degree of mobility and a wide range of motion to allow it to execute complex grasping motions in cooperation with the other fingers of the hand. The different, specially embodied joints of the thumb make a significant contribution to this mobility. A central role in this is played by the so-called "thumb saddle joint" (carpometacarpal joint) between the large multiangular bone (os trapezium) belonging to the wrist and the first metacarpal bone (os metacarpi). The two bones have a joint end shaped like a saddle and the joint surfaces of the bones are oriented at right angles to each other. This arrangement in the thumb saddle joint permits movements around two main axes oriented perpendicular to each other.

One of these movements that extends diagonally to the plane of the hand is referred to as opposition and reposition. In opposition, the thumb is situated opposite from the other fingers like a pair of tongs. In reposition, it lies in a plane with the fingers. The other movement includes the abduction and adduction of the thumb. Abduction refers to the spreading of the metacarpal section together with the thumb, while adduction refers to resting it against the hand in reposition or opposition. When the thumb is spread radially away from the index finger, it assumes a position of both reposition and abduction at the same time. If it is situated opposite from the other fingers with the palm spread (open pair of tongs), then it is in the abducted and opposed position in the saddle joint. Most thumb motions represent such combined motions around both axes of the saddle joint. Thus in circling motions of the thumb (circumduction) a combination of adduction, abduction, flexion, and extension occur. Opposition is understood to be a combined motion composed of adduction, flexion, and internal rotation of the thumb.

If the thumb saddle joint must be immobilized, it then becomes necessary to specifically limit or entirely prevent the movements involving the thumb saddle joint.

The prior art has disclosed a large number of thumb splints, but all of them suffer from an inability or limited ability to achieve the desired immobilization of the thumb saddle joint. For example, patent CH 690 954 has disclosed a thumb splint in which a sleeve for accommodating the thumb is provided, which is composed of two open thumb shells. The sleeve transitions into a palm part and a back-of-the-hand part, which enclose the hand only partially from the thumb side and are connected to each other by means of a flexible band that is guided around the outside of the edge of the hand. This splint configuration cannot effectively prevent motion in the abduction and opposition directions. The same is true for the metacarpal thumb splint from EP 0 143 348 and the splint from DE 30 06 362.

DE 35 19 493 has disclosed a thumb splint for immobilizing the thumb saddle joint and the metacarpophalangeal joint of the thumb, which is composed of a fixed shaped body that at least partially surrounds the thumb and the hand. The shaped body constitutes a clasp, which surrounds the hand and whose ends overlap in the regions of the hand oriented away from the thumb and can be connected to each other at the overlap point by a hook and loop fastener. The shaped body is embodied of one piece and is composed of a plastic. The clasp is immediately adjoined by a half-shell on the outside of the thumb, which shell is closed with a tensioning strap and is composed of a tongue that is formed onto the transition point between the clasp and half-shell and projects into the region between thumb and palm. After being closed, the clasp and half-shell exert pressure on the hand and thumb. The tongue provided to protect the saddle joint has a free end and therefore must be embodied as very stable in order to permit the required immobilization. The tongue prevents an adduction of the thumb, but not an abduction and in particular, not a movement between opposition and reposition. Furthermore, the tongue is uncomfortable because it cuts into the thumb and hand with its sharp lateral edges when the thumb is moved in the adduction direction.

Other thumb splints such as the ones known for example from U.S. Pat. No. 6,520,925 or U.S. Pat. No. 5,746,707 only immobilize the thumb against a flat support, which is as a rule insufficient for splinting the metacarpal region. The same is also true of the splints of the type disclosed in WO 2007/066367.

SUMMARY OF THE INVENTION

The object of the present invention, therefore, is to create a palmar thumb and thumb saddle joint splint, which permits a specific and complete immobilization of the thumb saddle joint, is simply constructed, can be put on easily without requiring special accessories, and is very comfortable to wear. In particular, the palmar thumb and thumb saddle joint splint should be usable in the treatment of rhizarthrosis and should prevent painful movements of joints affected by arthrosis.

This object is attained by all of the features of claim 1. The palmar thumb and thumb saddle joint splint according to the invention is characterized in that the first splint part for accommodating the thumb is embodied as a shell part, which is open at the top and is intrinsically stiff but plastically deformable by hand and into which the thumb can be laid; the first splint part is connected firmly to a hand edge part that is intrinsically stiff but plastically deformable by hand and, when the splint is put in place, embraces the edge of the splinted hand; and the fastening means include first and second immobilizing strips that are intrinsically stiff but plastically deformable by hand, with the first immobilizing strip extending from the hand edge part across the back of the hand to the first splint part and with the second immobilizing strip, starting from the hand edge part, being guided through between the thumb and index finger of the splinted hand to the first splint part.

In this way, the four fingers of the hand and the thumb are respectively attached to the hand edge part and the splint base element composed of the first splint part with a minimal degree of splint complexity, thus reliably preventing a movement of the two hand regions relative to each other by means of the thumb saddle joint.

One embodiment of the palmar thumb and thumb saddle joint splint according to the invention is characterized in that the first splint part is provided with an immobilizing tab, which is placed around the thumb resting in the first splint part and whose free end can be attached to the first splint part so that it is possible to prevent flexion of the metacarpophalangeal joint of the thumb.

Another embodiment of the palmar thumb and thumb saddle joint splint is characterized in that the hand edge part is composed of the same material as the first splint part and constitutes an extension of the first splint part.

Another embodiment is characterized in that the hand edge part is connected to an immobilizing tab which, when the splint is in place, extends across the back of the splinted hand and the second immobilizing strip is fastened to the immobilizing tab at one end.

Preferably, the immobilizing tab in this case is composed of the same material as the hand edge part and constitutes an extension of the hand edge part.

Another embodiment of the invention is characterized in that the first immobilizing strip is connected to the hand edge part at one end and to the first splint part at the other end.

In particular, the first immobilizing strip is detachably fastened at both ends and the fastening is embodied in the form of a hook and loop fastener.

Preferably, the detachable fastening of the second immobilizing strip to the palmar thumb and thumb saddle joint splint is also embodied in the form of a hook and loop fastener.

The ease of adaptation and high level of comfort when wearing the splint can be achieved in particular due to the fact that the elements of the palmar thumb and thumb saddle joint splint that are intrinsically stiff, but plastically deformable by hand are composed of a material that contains a core of transversely corrugated aluminum sheeting. Such a splint material is known for example from the patent WO 97/22312, whose material selection and dimensions of the corrugated sheet are expressly included herein by reference.

BRIEF DESCRIPTION OF THE DRAWINGS

The invention will be explained in detail below in conjunction with an exemplary embodiment shown in the drawings.

DETAILED DESCRIPTION OF THE INVENTION

Figure 1:
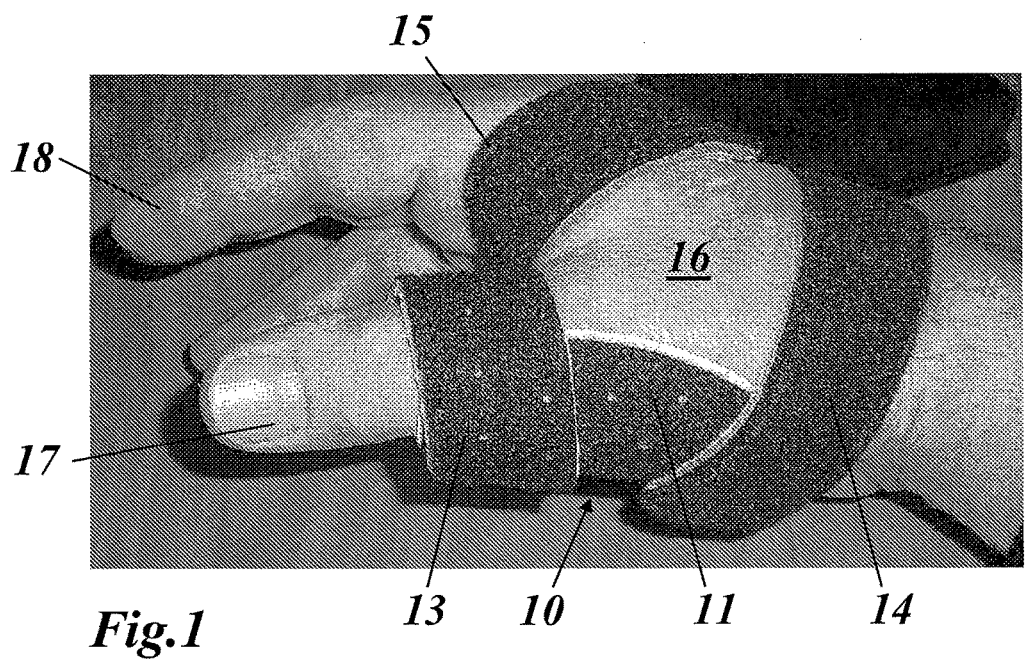
FIG. 1 is a side view of the use of a palmar thumb and thumb saddle joint splint according to an exemplary embodiment of the invention, with additional saddle joint immobilizing strips for immobilizing the thumb saddle joint.
Figure 2:
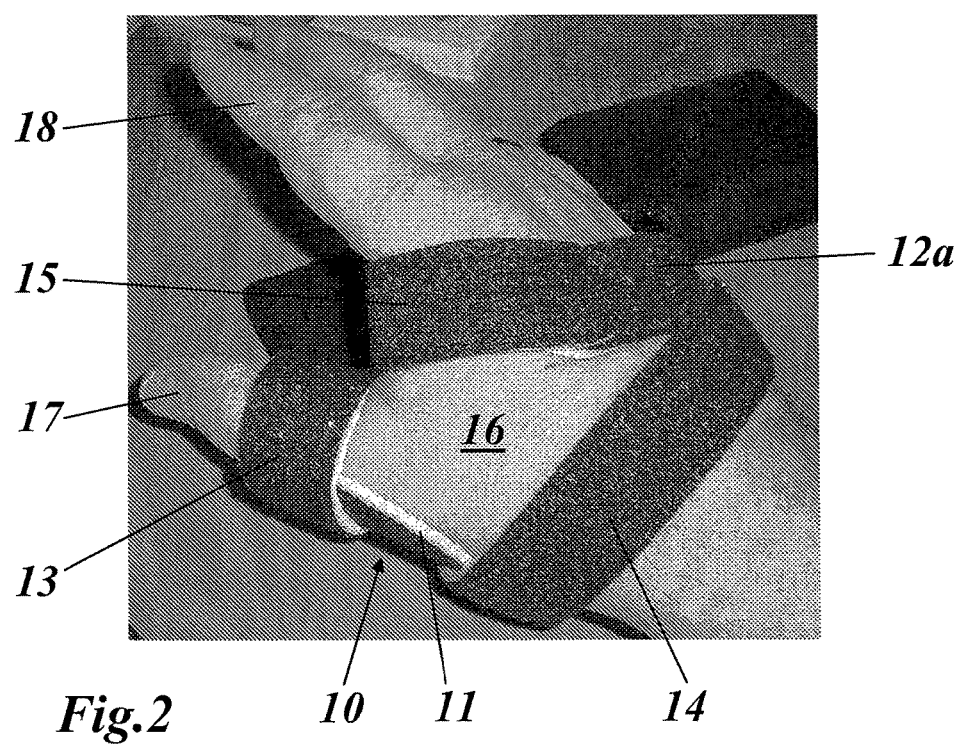
FIG. 2 shows the splinted hand from FIG. 1 viewed obliquely from above.
Figure 3:
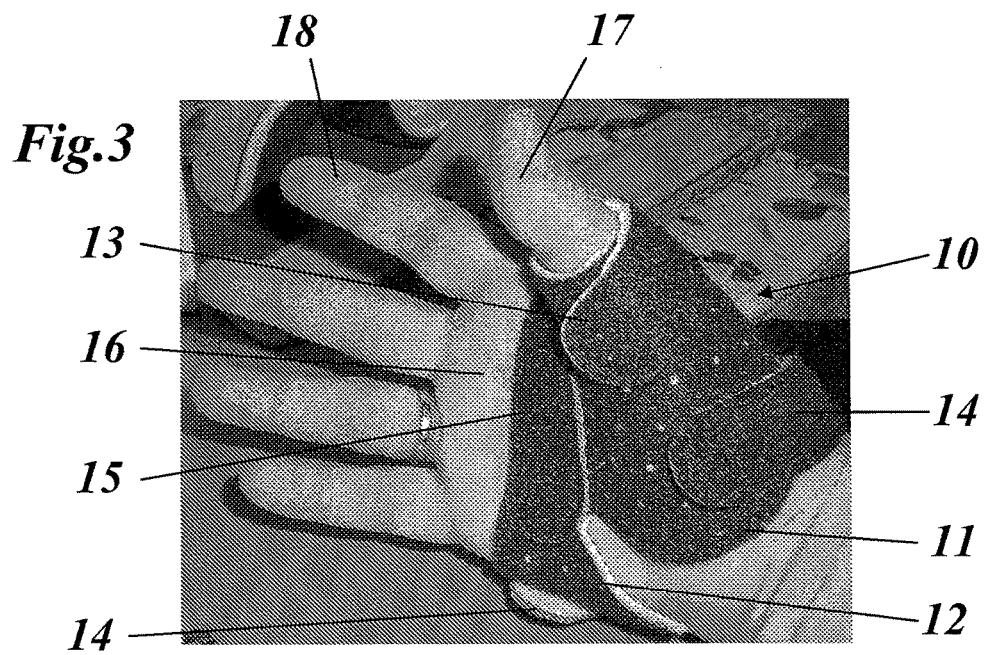
FIG. 3 shows the splinted hand from FIG. 1 viewed from below.
Figure 4:
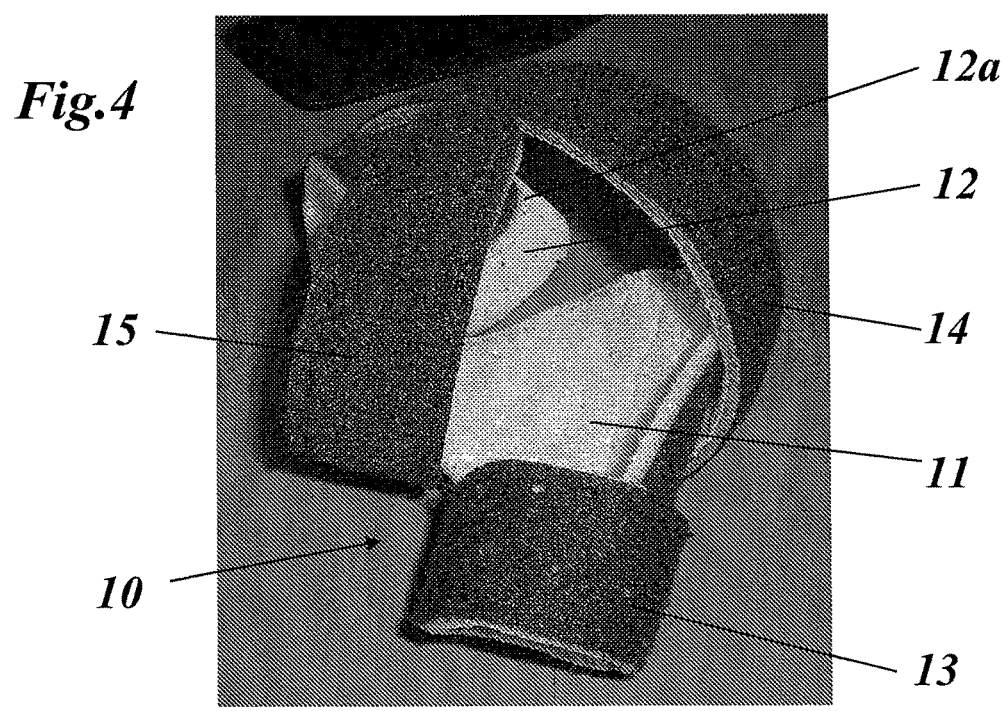
FIG. 4 shows the configuration of the splint in FIG. 1 when removed from the hand.

FIGS. 1, 2, and 3 show an exemplary embodiment of a palmar thumb and thumb saddle joint splint when used on a hand, shown from various viewing angles. FIG. 4 shows the same splint when it has been removed from the hand.

Figure 5:
FIG. 5 shows a core of transversely corrugated aluminum sheeting.

The base element of the palmar thumb and thumb saddle joint splint 10 shown in the figures is a first splint part 11, which is intrinsically stiff but plastically deformable by hand and into which the metacarpal region of the thumb 17 is inserted from above. Because it can be plastically deformed without additional accessories, the first splint part 11 can be adapted to the shape of the thumb 17 in order to achieve a comfortable, secure support of the thumb 17 in the metacarpal region. The intrinsic stiffness and plastic deformability are preferably achieved through the use of a splint material, which is described in detail in the above-mentioned WO 97/22312 and whose mechanical properties are based on the special properties of a transversely corrugated aluminum sheeting, such as shown in FIG. 5.

As shown in FIG. 4, the material of the first splint part 11 can advantageously be provided with (different) covering layers on both sides; in order to improve wearing comfort even with longer-term use, the side facing the skin is for example provided with skin-friendly, breathable upholstery, while the outside is advantageously provided with a covering material that can be part of a hook and loop fastener (by providing it with loops or hooks distributed over its surface). This covering material can in particular extend over the entire surface in order to permit additional elements to be attached by hook and loop fastener to arbitrary locations on the splint. Furthermore, the splint material and if need be, the immobilizing elements as well—as shown in the figures—can be provided with a perforation through which additional air can reach the splinted regions and through which perspiration from the skin can be conveyed to the outside.

For a first immobilization of the thumb 17 in the formed first splint part 11, the first splint part 11 is provided with an immobilizing tab 13 extending perpendicular to the longitudinal direction of the thumb; this immobilizing tab is placed around the thumb 17 lying in the splint part 11 and its free end can be attached to the first splint part 11 (primarily shown in FIG. 1). The immobilizing tab 13 can, for example, be composed of a conventional flexible belt material. Preferably, the immobilizing tab 13 can be attached to the first splint part 11 by means of a hook and loop fastener that takes advantage of the properties of the outer covering layer of the first splint part 11. Since the width of the immobilizing tab 13 is relatively small compared to the first splint part 11, the distal phalanx of the thumb 17 has a sufficient freedom of movement in the first splint part (11) despite this immobilization.

As an additional element, the palmar thumb and thumb saddle joint splint 10 has a second splint part in the form of a hand edge part 12 clearly shown in FIGS. 3 and 4, which is integrally joined to the first splint part 11 in a single unit and when in place, laterally encloses the edge of the splinted hand 16. The first splint part 11 and hand edge part 12 together constitute a support surface for the hand 16 and thus in a first step, immobilize the position of the splinted thumb 17 relative to the hand 16. The hand edge part 12 is composed of the same material as the splint part 11 and therefore has the same property of being intrinsically stiff, but plastically deformable by hand so that it can be easily and permanently adapted to the shape of the particular hand.

The hand edge part 12 transitions into another immobilizing tab 12a, which extends across the back of the splinted hand 16 when the splint is in place (in particular see FIG. 2), and is composed of the same material—which is intrinsically stiff, but plastically deformable by hand—as the hand edge part 12. As shown clearly in FIGS. 2 and 3, the four fingers of the rest of the hand are attached to the palmar thumb and thumb saddle joint splint 10 by means of an immobilizing strip 15 that is intrinsically stiff, but plastically deformable by hand and is guided between the thumb 17 and index finger 18 of the splinted hand 16 and detachably fastened to the palmar thumb and thumb saddle joint splint 10. The detachable fastening of the immobilizing strip 15 to the palmar thumb and thumb saddle joint splint 10 is preferably once again embodied in the form of a hook and loop fastener, with the one end advantageously being fastened to the immobilizing tab 12a (FIG. 2).

Another base element of the palmar thumb and thumb saddle joint splint 10 in addition to the first splint part 11 and the hand edge part 12 is an immobilizing strip 14 that is likewise intrinsically stiff, but plastically deformable by hand and is guided across the back of the splinted hand 16 (in particular see FIG. 2). The immobilizing strip 14 is embodied as a separate part and is detachably fastened at both ends to the first splint part 11 and the hand edge part 12, respectively; once again, the fastening is embodied in the form of a hook and loop fastener. Since the immobilizing strip 14—unlike a flexible fastening band of a conventional type—is itself composed of splinting material, it can be adapted in the same way to the shape of the particular hand and makes a significant contribution to the immobilizing action. In particular, it immobilizes the thumb 17 resting in the first splint part 11 relative to the rest of the hand. The two immobilizing strips 14 and 15 thus—separately—immobilize, respectively, the four fingers of the hand and the thumb in the splint composed of the parts 11 and 12 so that all possible movement in the metacarpophalangeal joint of the thumb and in the thumb saddle joint, in particular even movement in the opposition and reposition directions, is securely and comfortably prevented.

All in all, the invention produces a palmar thumb and thumb saddle joint splint that permits a local, targeted immobilization of the thumb saddle joint, particularly also in cases of rhizarthrosis, is easy to use, can also be used without additional accessories even in emergencies, and features a high degree of wearing comfort.

It is, however, also conceivable for the first and second immobilizing strips 14 and 15 to be embodied not of a material that is intrinsically stiff while still plastically deformable by hand, but instead in the form of cloth bands. In this case, the splint 10 still immobilizes the metacarpophalangeal joint of the thumb and can be advantageously used as a palmar thumb splint.

The invention claimed is:

1. A palmar thumb and thumb saddle joint splint (10) for fastening to a hand, comprising:
    a first splint part (11) for receiving a thumb and comprising a shell part, which is intrinsically stiff but plastically deformable manually and into which the thumb can be laid;
    a hand edge part (12) connected firmly to the first splint part (11), the hand edge part (12) intrinsically stiff but plastically deformable manually and, when the splint is in place, is adapted to curve around an edge of the hand that is opposite the thumb, wherein the first splint part (11) and the hand edge part (12) form a support surface for a palm of the hand and that has an open top to receive the hand; and
    a fastening means (14,15) for fastening the first splint part (11) to the hand including first and second immobilizing strips (14, 15) which are intrinsically stiff but plastically deformable manually,
    the first immobilizing strip (14) extending from the hand edge part (12) to the first splint part (11) and over the open top, wherein the first immobilizing strip (14) is adapted to extend across a back of the hand, and
    the second immobilizing strip (15) extending from the hand edge part (12) to the first splint part (11) and over the open top, wherein the second immobilizing strip (15) is adapted to extend across the back of the hand and between the thumb and index finger of the hand to the first splint part (11).

2. The palmar thumb and thumb saddle joint splint as recited in claim 1, wherein the first splint part (11) is provided with an immobilizing tab (13), which is adapted to extend around and immobilize the thumb lying in the first splint part (11) and whose free end can be attached to the first splint part (11).

3. The palmar thumb and thumb saddle joint splint as recited in claim 2, wherein the hand edge part (12) is attached to another immobilizing tab (12a), which, when the splint is in position, is adapted to extend across the back of the hand, and one end of the second immobilizing strip (15) is fastened to the another immobilizing tab (12a).

4. The palmar thumb and thumb saddle joint splint as recited in claim 3, the another immobilizing tab (12a) is composed of the same material as the hand edge part (12), constitutes an extension of the hand edge part (12), and extends at an angle with respect to the first immobilizing strip (14).

5. The palmar thumb and thumb saddle joint splint as recited in claim 1, wherein the hand edge part (12) comprises the same material as the first splint part (11) and constitutes an extension of the first splint part (11).

6. The palmar thumb and thumb saddle joint splint as recited in claim 1, wherein the first immobilizing strip (14) is fastened at the one end to the hand edge part (12) and is fastened at the other end to the first splint part (11).

7. The palmar thumb and thumb saddle joint splint as recited in claim 6, wherein the first immobilizing strip (14) is detachably fastened at both ends with a hook and loop fastener.

8. The palmar thumb and thumb saddle joint splint as recited in claim 1, wherein the second immobilizing strip (15) comprises a hook and loop fastener.

9. The palmar thumb and thumb saddle joint splint as recited in claim 1, wherein elements (11, . . . , 15) of the palmar thumb and thumb saddle joint splint (10) that are intrinsically stiff but plastically deformable manually comprise a material that contains a core of transversely corrugated aluminum sheeting.

* * * * *